United States Patent [19]
Lawrence

[11] Patent Number: 5,378,889
[45] Date of Patent: Jan. 3, 1995

[54] METHOD AND APPARATUS FOR DETECTING HYDROCARBON FUELS IN A VAPOR STATE WITH AN ABSORBER-EXPANDER MEMBER

[75] Inventor: William R. Lawrence, Dickinson, Tex.

[73] Assignee: California Lightwave Laboratories, Inc., Downieville, Calif.

[21] Appl. No.: 125,259

[22] Filed: Sep. 23, 1993

[51] Int. Cl.⁶ .................................................. H01J 5/16
[52] U.S. Cl. ................................. 250/227.16; 356/437
[58] Field of Search ................... 250/227.16, 227.21, 250/227.14, 227.11; 385/12, 123, 126, 145; 356/437, 440

[56] References Cited

U.S. PATENT DOCUMENTS

| | | |
|---|---|---|
| 4,270,049 | 5/1981 | Tanaka et al. . |
| 4,590,462 | 5/1986 | Moorehead . |
| 4,596,443 | 6/1986 | Diemeer et al. . |
| 4,842,783 | 6/1989 | Blaylock . |
| 4,892,383 | 1/1990 | Klainer et al. ............... 250/227.21 |
| 5,015,843 | 5/1991 | Seitz et al. . |
| 5,138,153 | 8/1992 | Gergely et al. . |
| 5,144,690 | 9/1992 | Domash . |
| 5,164,588 | 11/1992 | Marcus . |
| 5,168,156 | 12/1992 | Fischer et al. . |
| 5,240,643 | 8/1993 | Buckley et al. ............... 385/12 |

*Primary Examiner*—David C. Nelms
*Assistant Examiner*—Que T. Le
*Attorney, Agent, or Firm*—Flehr, Hohbach, Test, Albritton & Herbert

[57] ABSTRACT

A method and apparatus for detecting the presence of hydrocarbon analyte in at least one of a liquid and vapor state. The apparatus (21) includes an optical fiber (22), an absorber-expander (31) mechanically coupled (32) to the optical fiber (22) to produce a change in transmission of light along the fiber (22) upon absorption of the hydrocarbon (33). The absorber-expander (31) is selected to absorb hydrocarbons, but not water, and to be capable of multiple reversible expansion and contraction cycles without significant structural degradation. Methyl terminated, silica and iron oxide filled, dimethyl polysiloxane provides a material which will experience substantial swelling in the presence of a hydrocarbon and yet is substantially reversible on desorption of the hydrocarbon from the absorber-expander (31). The method includes positioning an optical fiber (22) having such an absorber-expander (31) for absorption of hydrocarbons and detecting the decrease in light transmission produced by expansion of the absorber-expander (31), for example, by one of microbending and axial misalignment. The location of the absorber-expander (31) along strand (22) can be determined by optical time domain reflectometry or by digital sensing nodes (122), and multiple couplings (57) and biasing couplings (153) for mounting the absorber-expanders (152) to the optical fiber (151) can be used to enhance sensitivity.

50 Claims, 4 Drawing Sheets

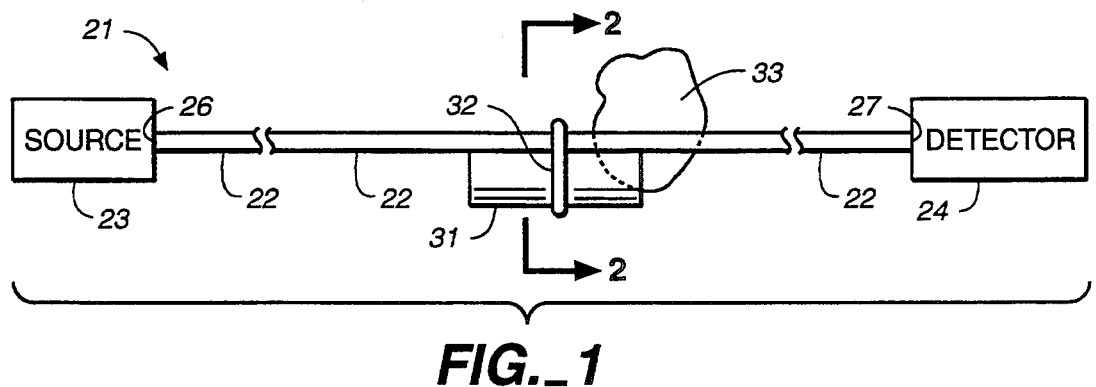
FIG._1
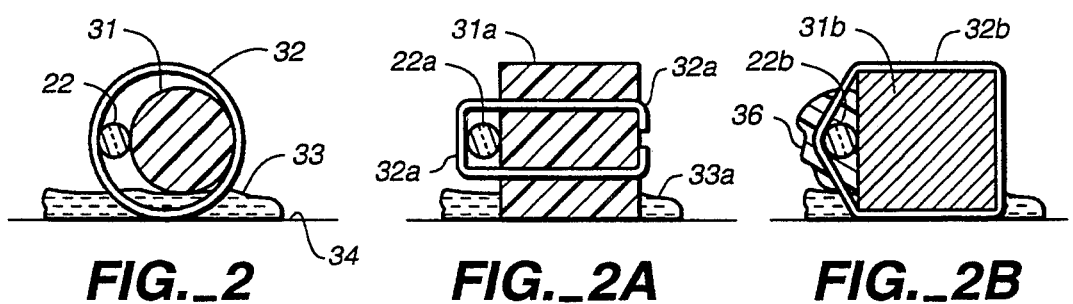
FIG._2  FIG._2A  FIG._2B
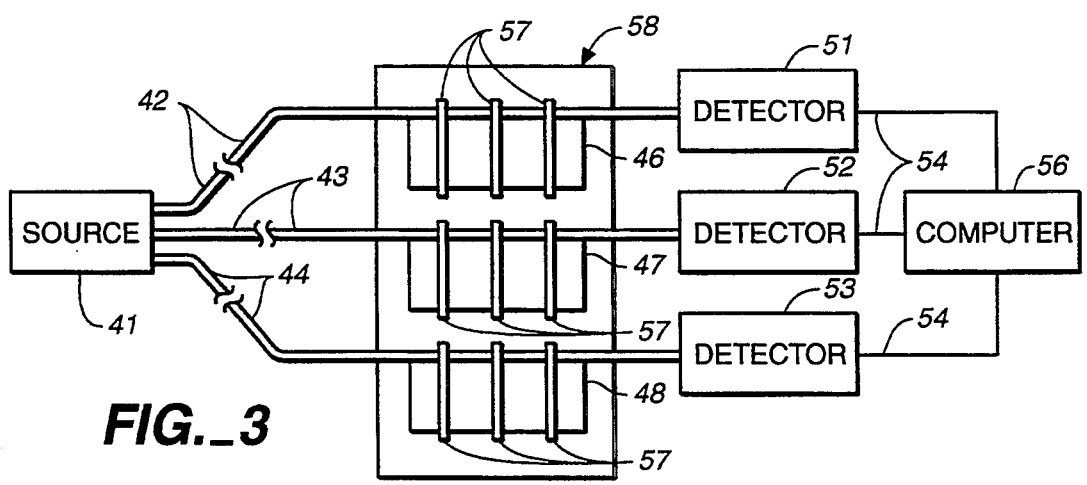
FIG._3

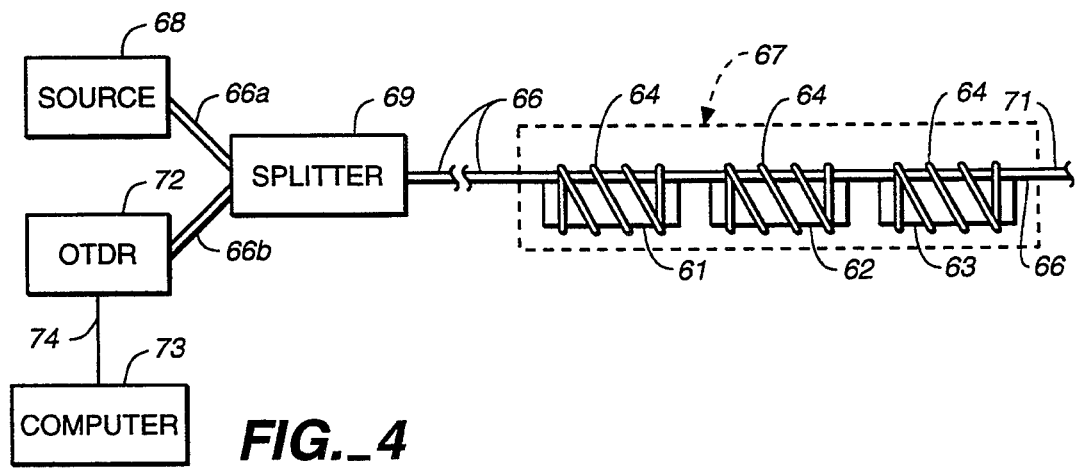
FIG._4
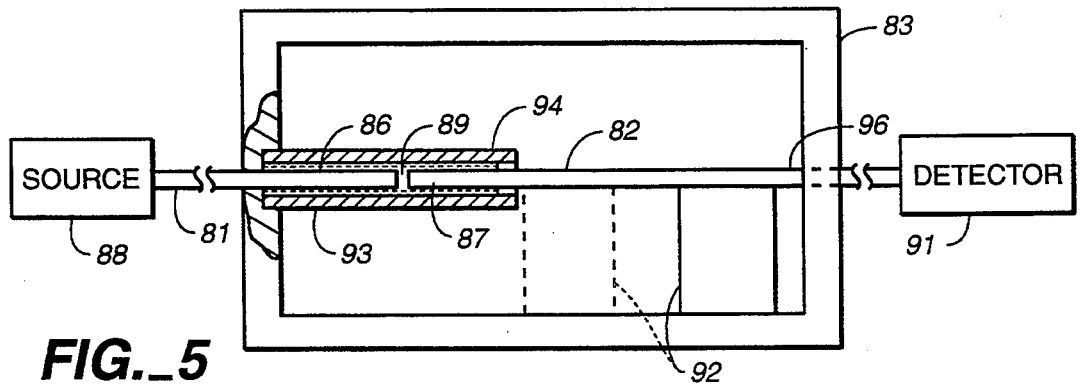
FIG._5
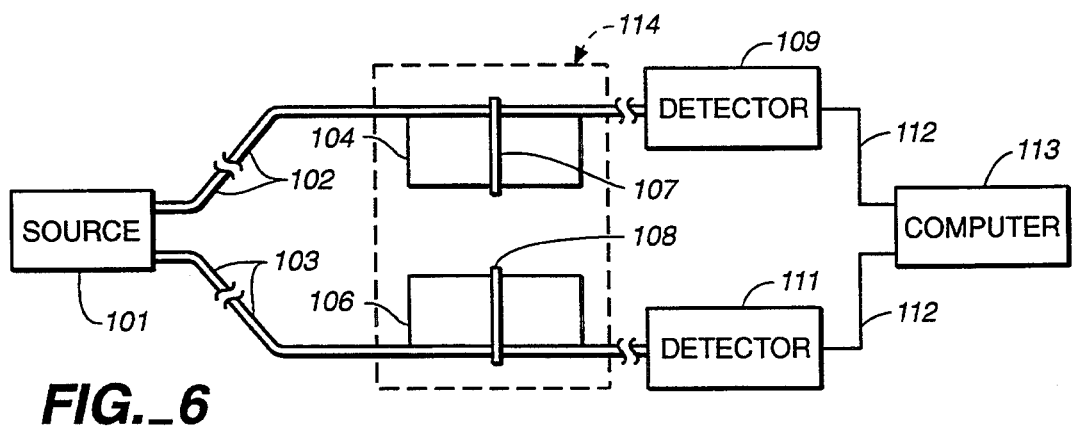
FIG._6

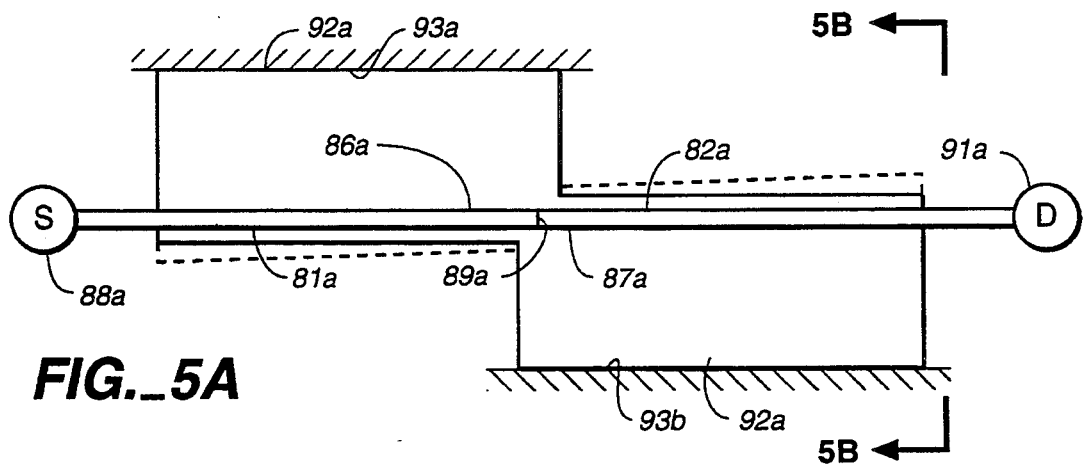
FIG._5A
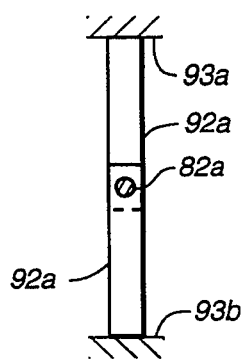
FIG._5B
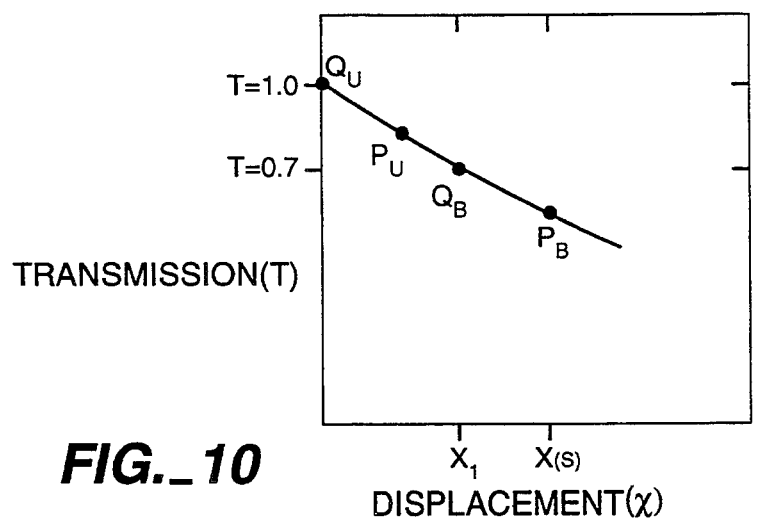
FIG._10
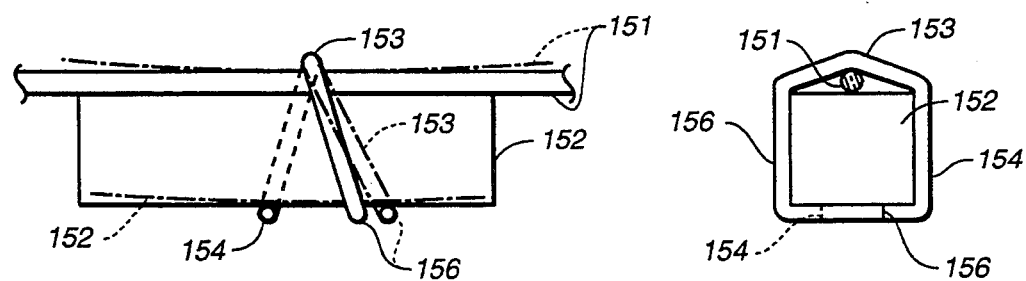
FIG._8
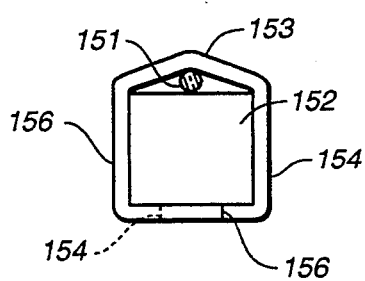
FIG._9

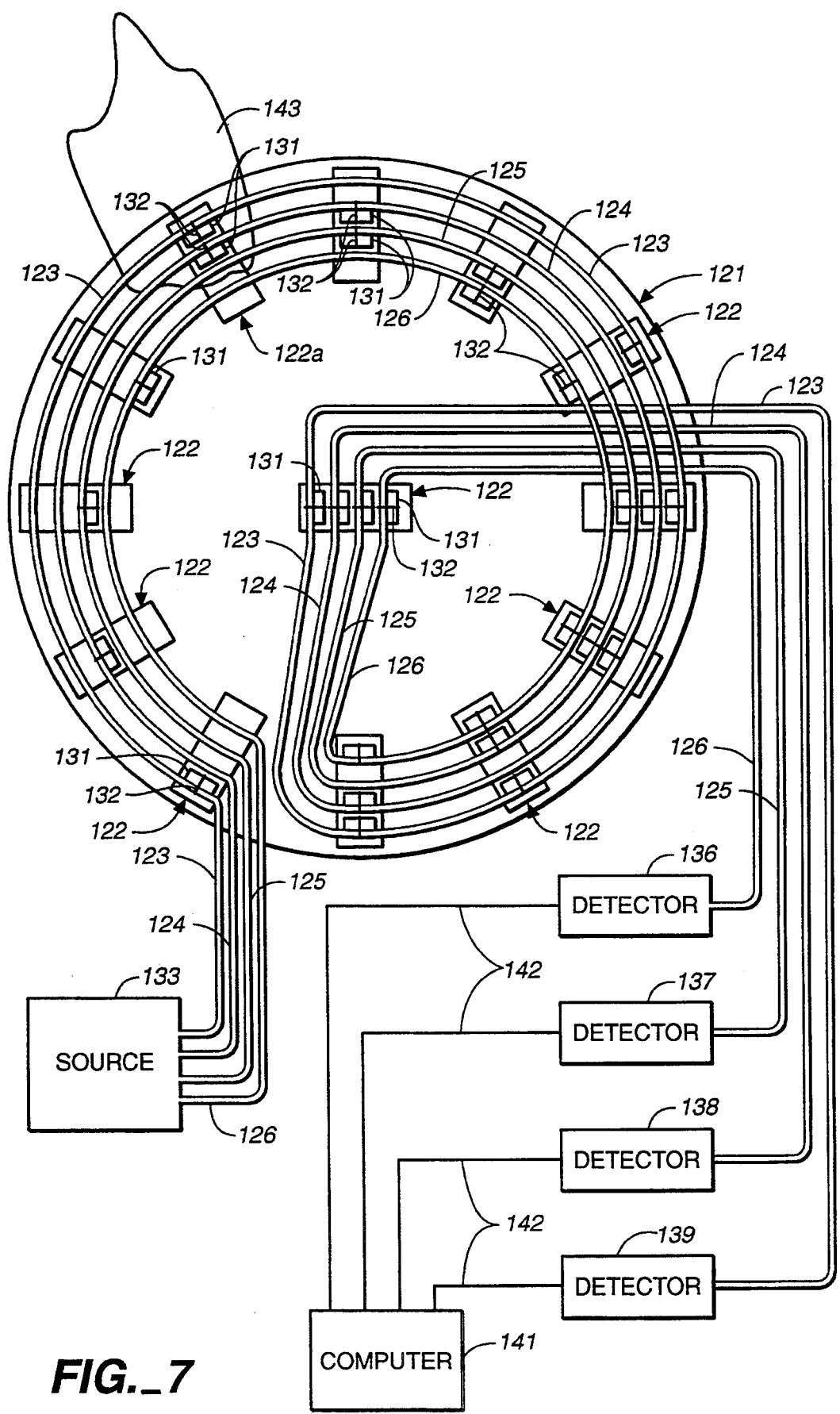
FIG._7

METHOD AND APPARATUS FOR DETECTING HYDROCARBON FUELS IN A VAPOR STATE WITH AN ABSORBER-EXPANDER MEMBER

TECHNICAL FIELD

The present invention relates, in general, to the detection of hydrocarbon analytes in either a liquid or vapor state, and more particularly, relates to a method and apparatus for the detection of hydrocarbon fuels employing microbending of an optical fiber or misalignment of fiber portions and optical time domain reflectometry.

BACKGROUND ART

The detection or sensing of hydrocarbon fuels, such as diesel oil, gasoline and Jet-A fuel leaking from storage tanks has received considerable attention. These hydrocarbon fuels are stored in substantial volume in above ground and below ground storage tanks and present a significant hazard to safety and health if they leak into the surrounding environment.

Two approaches have generally been taken to the problem of hydrocarbon fuel leakage. First, storage tanks may be constructed with double bottoms so that leakage from the inner tank is caught and contained by the outer bottom wall. This approach is very expensive and is often impractical in retrofitting situations. The second approach is to provide detection or sensing apparatus proximate the storage tanks which are capable of sensing leaking fuel from the tanks. Upon detection of leaking fuel, the source of the leak can be found and repaired. These approaches also may be used together.

The detection of leaking hydrocarbon fuels, however, is not without considerable problems. Tanks themselves often are very large and situated in even larger tank farms, making it necessary for a multiplicity of detectors to be used and a premium to be placed on locating the source of the leak. As a plurality of discrete detection apparatus are employed, the detection costs rise rapidly. If multiple detectors are not used, sufficient oil may leak to the surrounding environment so as to present a substantial health and/or safety hazard before detection occurs. Moreover, as more fuel escapes the location of the leak will be more difficult to determine.

Hydrocarbon leak detecting apparatus often have been constructed in a manner which requires their replacement or repair upon detection of a leak, that is, once contacted by a hydrocarbon fuel, the detection device, or its key components, must be replaced before the detector can be used again. Another problem is that in most storage tank farms, there will be considerable ground water present, and any detector must be capable of distinguishing between ground water and hydrocarbons and capable of functioning without being overwhelmed by ground water in order to avoid false detection signals. Finally, most hydrocarbon detectors are based upon sensing hydrocarbons in either a vapor state or a liquid state, but not both. The vapor-based sensors, therefore, tend to be overrun by ground water and liquids, and the liquid-base sensors tend to be insensitive to the presence of vapor.

In recent years, many attempts have been made to employ the unique and varied light transmission properties of optical fibers in detecting apparatus. In communication cable applications, the microbending of an optical fiber has been used to detect the location of moisture or ground water entering the cable. In U.S. Pat. No. 4,596,443 to Diemeer, et al., an unspecified swelling agent is positioned inside the cable and is mechanically coupled to press a ribbed-shaped pattern against the optical fiber upon swelling of the agent. Optical time domain reflectometry or a back-scatter technique is used to locate the position of the microbend along the fiber, and thus the position of water leaking into the cable. Such a system, however, is designed for sensing the presence of water, rather than to be insensitive to water and to detect the presence of hydrocarbon fuels. Reversibility of the swelling agent's expansion also is not suggested or disclosed in the Diemeer, et al. patent.

U.S. Pat. No. 4,590,462 to Moorehead also employs microbending of an optical fiber in a detection unit, and the Moorehead device is used to detect hydrocarbon fuels. A rotary actuator is mechanically coupled to an optical fiber to produce microbending of the fiber. The rotary actuator includes a spring mechanism having stored energy which is released upon degradation of shear pins under the action of hydrocarbons. Thus, when the hydrocarbon analyte is present in sufficient quantity to degrade the shear pins, the spring is released and the optical fiber displaced to produce a microbend that can be sensed by optical time domain reflectometry. This approach, however, clearly is not reversible since it depends upon destruction of the shear pins upon contact with the hydrocarbon.

A number of prior art fiber optic-based detector systems have been based upon the coupling of the evanescent wave traveling down the exterior of the fiber optic core. Thus, U.S. Pat. Nos. 4,270,049, 5,138,153, 5,144,690 and 5,168,156 are all based on evanescent wave phenomenon. In the patent to Tanaka et al., U.S. Pat. No. 4,270,049, a fiber optic sensor assembly is employed in which the light transmitted down the fiber optic core is reduced in intensity due to adhesion of an analyte, such as a hydrocarbon fuel, to the core. The core is clad with material having an index of refraction which is less than the core index of refraction, and contact and adhesion of the analyte to the cladding results in an increase in clad index of refraction which results in a reduction in the light transmitted along the core. The Tanaka et al. patent also teaches the use of silicon resins as a cladding which will be damaged or broken down by hydrocarbons.

In U.S. Pat. No. 5,138,153 to Gergely et al., a distributed fiber optic sensor based upon evanescent effects is disclosed in which the cadding has an index of refraction less than the core and the cladding is sensitized to the analyte. When the analyte contacts the cladding, it increases the index of refraction of the cladding above the core to thereby couple the light transmitted in the core to the evanescent wave. The Gergely et al. patent employs its sensor system in a hydrocarbon tank farm, but the cladding is selected to undergo an increase in the index of refraction. Optical time domain reflectometry is used to locate leaks, and both continuous and pulsed light can be employed to sense liquids and vapors having analytes which will react with the cladding. The patent to Gergely et al., however, has no disclosure as to cladding materials which are suitable for use on the fiber optic strand.

U.S. Pat. No. 5,144,690 to Domash discloses a fiber optic sensor system in which coating patterns are provided which induces strain on a dual core optical fiber. Evanescent wave coupling between cores is sensed.

This system is not disclosed as being intended for hydrocarbon fuel detection.

U.S. Pat. No. 5,168,156 to Fischer et al. employs a fiber optic sensor assembly in which three fibers are used with one acting as an input, and the other two acting as a reference fiber and a signal fiber. The three fibers are coupled together optically and the sensor fiber is stripped with cladding and exposed to an analyte to be sensed. Light attenuation as a result of the analyte affect on the evanescent wave on the unclad fiber is detected as compared to the reference fiber, which is clad and shielded from the analyte.

Fiber optic detectors also have been based upon the interpositioning of a sensor material along the length of a fiber optic core so that transmission and/or reflection measurements will indicate when an analyte is present at the material interposed along the core. U.S. Pat. Nos. 4,842,783, 5,015,843 and 5,164,588 are examples of this approach. In U.S. Pat. No. 4,842,783 to Blaylock, a fiber optic sensor assembly is provided in which a polymeric gel is cross-linked in situ onto the end of the fiber and a dye absorbed into the gel, which preferably is swellable to absorb the dye. The dye in the gel is selected to be responsive to an analyte to be sensed. The dye, for example, can be fluorescent but the system is not designed for use with hydrocarbons. Dyes, however, tend to be suitable only in irreversible chemical reaction which require replacement of the sensor once the analyte is exposed to it.

U.S. Pat. No. 5,015,843 to Seitz et al. is directed to a fiber optic system in which polymer swelling is used to mechanically or physically displace a reflective surface coupled to the fiber optic core and thereby influence light transmission back to the detector. The system requires a relatively high concentration of analyte to be effective, and in order to enhance a sensitivity and minimize this disadvantage, the system preferably is miniaturized. Numerous polymers are discussed for sensing various products, none is disclosed as being reversible in its reaction with hydrocarbon fuels.

In U.S. Pat. No. 5,164,588 to Marcus, a distributed sensor system is provided in which reflector/transmission couplings and analyte sensors are interposed in series and alternating along an optical fiber strand. Light pulses pass through the sensors, and in part through the connectors and in part back to a detector, and the pulses can be used to detect environmental or analyte effects on the sensors. Many analytes may be sensed but hydrocarbon fuel sensing is not disclosed.

Notwithstanding the success of the various optical fiberbased detectors in detecting a wide range of analytes, detecting the presence of liquid and/or vapor hydrocarbon fuels, and distinguishing the same from ground water, by a detector system which is reversible and reusable through many cycles without significant hysteresis loss remains a substantial problem.

An alternative to optical fiber detection has also been employed which is currently being marketed under the trademark GORE-TEX cable, for example, by W. L. Gore and Associates of Phoenix, Ariz. The GORE-TEX coaxial cable has a hydrocarbon fuel absorbent media (expanded PTFE) situated between a central conductor and an outer, perforated, cylindrical conductor or shield. Pulses of RF energy are transmitted down the coaxial cable and are reflected back at the location of absorbed hydrocarbon. Time domain reflectometry is used to locate the position along the cable at which hydrocarbons are absorbed.

The GORE-TEX cable, however, cannot distinguish between Jet-A, gasoline or diesel fuel. It will not detect hydrocarbons in a vapor state, it cannot generate an analog output signal, and it has location resolution and distance range limitations.

Accordingly, it is an object of the present invention to provide an apparatus and method for detecting the presence of hydrocarbon fuels in either a liquid or a vapor state which can discriminate between such fuels and water and is suitable for use for multiple detection cycles.

A further object of the present invention is to provide a hydrocarbon fuel detection apparatus and method which is easy to install, requires minimum maintenance, is inexpensive to construct, is easily adjusted and can differentiate between different hydrocarbon fuels and can distinguish such fuels from ground water.

The hydrocarbon fuel detection apparatus and method of the present invention has other objects and features of advantage which will become apparent from, and are set forth in more detail in, the accompanying drawing and the following description of the Best Mode of Carrying Out the Invention.

DISCLOSURE OF INVENTION

A method for detecting the presence of a hydrocarbon in at least one of a liquid and vapor state is provided which is comprised, briefly, of the steps of selecting an absorber-expander material which is hydrophobic and yet absorbs hydrocarbon fuels and expands by a significant amount. The absorber-expander member must be capable of multiple expansion and contraction cycles in the presence and absence of the hydrocarbon analyte, in either a liquid or vapor state, while remaining substantially undegraded, and red silicone rubber meets these criteria. The next step is to mechanically couple the silicone rubber member to a fiber optic strand in a manner producing a decrease in light intensity transmitted along the strand, for example by microbending of the strand upon expansion of the silicone rubber member or axial misalignment of strand portions. Finally, the method includes the step of optically coupling detection apparatus to the strand for detection of the occurrence of a reduction in light transmission along the strand.

The detection apparatus of the present invention is comprised, briefly, of an optical fiber, and an absorber-expander mechanically coupled to the optical fiber to produce a change in transmission of light along the fiber upon absorption of a hydrocarbon, with the absorber-expander being formed from a hydrophobic hydrocarbon-absorbing rubber material selected to expand upon absorption of the hydrocarbon and retain sufficient structural integrity to permit repetitive expansion and contraction cycles, and detection apparatus optically coupled to the fiber for detection of a change in light transmission in the fiber due to microbending.

DESCRIPTION OF THE DRAWING

FIG. 1 is a top plan, schematic representation of a hydrocarbon detection apparatus constructed in accordance with the present invention.

FIG. 2 is an enlarged end elevation view, in cross section, taken substantially along the plane of line 2—2 in FIG. 1.

FIG. 2A is a cross-sectional view corresponding to FIG. 2 of an alternative embodiment of the apparatus of FIG. 1.

FIG. 2B is a cross-sectional view corresponding to FIG. 2 of still a further alternative embodiment of the apparatus of FIG. 1.

FIG. 3 is a top plan, schematic representation of an alternative embodiment of the detector apparatus of the present invention.

FIG. 4 is a top plan, schematic representation of still a further alternative embodiment of the detector apparatus of the present invention.

FIG. 5 is a side elevation view, partially in cross-section, of another alternative embodiment of the detector apparatus of the present invention.

FIG. 5A is a schematic side elevation view of a further alternative embodiment of the detector apparatus of the present invention.

FIG. 5B is an end elevation view of the apparatus of FIG. 5A taken substantially along the plane of line 5B—5B in FIG. 5A.

FIG. 6 is a top plan, schematic representation of still another alternative embodiment of the apparatus of the present invention.

FIG. 7 is a top plan, schematic representation of an assembly of detectors constructed in accordance with the present invention and arranged to provide digital location signals FIG. 8 is a fragmentary side elevation view of an alternative embodiment of the apparatus of the present invention suitable for adjustable biasing of the detector sensitivity.

FIG. 9 is an end elevation view of the apparatus of FIG. 8.

FIG. 10 is a graphical representation of transmissivity versus displacement for the apparatus of FIG. 8.

BEST MODE OF CARRYING OUT THE INVENTION

The hydrocarbon analyte detection apparatus of the present invention is constructed in a manner which allows it to be capable of distinguishing hydrocarbons from water, in both liquid and vapor states, and to be capable of multiple detection and restoration cycles. Thus, the present detector and method do not require extensive repair or replacement of components upon detection of the target hydrocarbon analyte, such as hydrocarbon fuels. This allows the detection apparatus of the present invention to be positioned in difficult to access locations with little or no repair or replacement being required. Once the leaking hydrocarbon analyte has been contained and removed through absorption, evaporation and/or other techniques, the present detection apparatus will automatically evaporate absorbed hydrocarbons and be restored to a condition capable of detecting the next instance of spilling or leaking at the detector location.

Referring now to FIG. 1, a detection apparatus, generally designated 21, is shown. The present detection apparatus includes an optical fiber or strand 22 which is optically coupled to a source of light energy 23 and is further optically coupled to a detection apparatus or detector 24. While illustrated in FIG. 1 in an arrangement in which source 23 is coupled to end 26 of fiber 22 and detector 24 is coupled to opposite end 27 of fiber 22, it will be understood that using conventional fiber optic techniques the detector and source can be coupled to the same end of the fiber.

The composition of fiber 22, the components in source 23 and detector 24 are not regarded as a novel portion of the present invention, and they are well-known in the fiber optic industry. Source 23, for example, can be a LED source, a laser, or incandescent light bulb. Detection apparatus 24 is shown in FIG. 1 as a light sensing apparatus capable of sensing a decrease in light flux transmitted from source 23. Such detection apparatus, for example, is commercially manufactured by EG and G Vactec of St. Louis, Mo. and sold under Model No. VTP 8440. Optical fiber strand 22 can be any typical communications optical fiber.

In order to produce a detectable decrease in light intensity sensed by detector 24, detection apparatus 21 of FIG. 1 includes an absorber-expander member 31 mechanically coupled, in this case by ring member 32, to fiber 22 in a manner which will produce microbending of fiber 22 upon absorption of a hydrocarbon analyte. In the embodiment shown in FIG. 5, an absorber-expander is coupled to one of two portions of an optical fiber in order to decrease the transmitted light intensity by misaligning the axes of the fiber portions.

The selection of absorber-expander 31 is a very important feature of the present invention, whether microbending or misalignment are produced by expansion of the absorber-expander. The absorber-expander must be able to distinguish between ground water and hydrocarbons in both liquid and vapor states. It must be reversible, that is, capable of multiple expansion and contraction cycles upon absorption of hydrocarbon and then subsequent desorption of the hydrocarbon from the absorber-expander.

The problem of selecting an absorber-expander material 31 which is capable of multiple cycles of expansion and contraction is substantial since many compounds are attacked by hydrocarbon analytes and particularly hydrocarbon fuels. Thus, these fuels act as a solvent and/or cause serious degradation of numerous potential absorber-expander materials.

It has been found, however, that dimethyl polysiloxane rubber, which is methyl terminated and has silica and iron oxide fillers, is not only hydrophobic, which is required to prevent ground water absorption, but it is capable of absorbing many hydrocarbon fuels. Moreover and very importantly, such silicone rubber expands upon absorption of hydrocarbons and contracts as the fuel leaves or is desorbed leaving the absorber-expander in substantially its original condition. Methyl terminated, and silica and iron oxide filled, dimethyl polysiloxane is commercially distributed under the name of Red Silicone Rubber and is produced commercially by companies such as General Electric Company through its GE Silicone division.

Red Silicone Rubber can be cast or extruded in virtually any shape to produce a self-supporting member that is easily coupled to fiber optic strand 22. Silicone rubber will not absorb water, and accordingly, it is capable of detecting hydrocarbon fuels even when buried in ground which periodically or perennially has substantial ground water. This absorber-expander material can even be used in a water environment. When Red Silicone Rubber is exposed to the hydrocarbon fuels such as gasoline, diesel oil, Jet-A fuel, either in a liquid or a vapor state, such hydrocarbons will be absorbed and produce substantial expansion of the member 31. Thus, as much as 40% expansion will occur when Red Silicone Rubber is allowed to absorb gasoline, 35% when absorbing diesel and 20% when absorbing Jet-A fuel.

As shown in FIGS. 1 and 2, therefore, a body of hydrocarbon analyte or fuel 33 can be seen to contact or be in sufficiently close proximity to absorber-expander 31 that liquid and/or vapor will be absorbed by member 31. Such absorption produces substantial expansion of member 31, which in turn is confined by containment or coupling ring 32. The result is that the fiber 22 is bent upwardly, as viewed in FIG. 1, and to the left, as viewed in FIG. 2, by the expansion of member 31 through absorption of hydrocarbon 33. The microbending at coupling ring 32 will result in a reduction in the amount of light transmitted from source 23 to detector 24. Thus, the sensing of a decrease in light transmission by detector 24 can be used to detect the presence of a hydrocarbon analyte at absorber-expander 31. In order to be able to detect fuel leakage around large storage tanks or in tank farms, a plurality of detectors constructed as shown in FIG. 1 could be used, but it is preferable to distribute a plurality of members 31 along the length of a common optical fiber 22. Thus, members 31 can be secured by coupling rings 32 along the length of a fiber optic strand 22 which is positioned adjacent and/or under hydrocarbon fuel storage tank. The presence of leaking fuel at any of the discrete detectors will cause expansion of the Red Silicone Rubber members 31 and microbending of the fiber optic strand. Detector 24 can sense the occurrence of microbending somewhere along the strand and an optical time domain reflectometry detector, schematically shown in FIG. 4, can be used to determine which absorber-expander is sensing a leak.

As shown in FIG. 2, the fuel leak 33 is supported on a surface 34 which is impervious to the fuel. This condition can occur, for example, when the tank is surrounded by a fuel-impervious surface, but in many instances, surface 34 will be porous to fuel 33, and the fuel will not migrate from the storage tank to a position above the ground until the quantity of fuel leaking is substantial. Thus, the ability to absorb vapor coming up through a porous surface 34 allows the detector of the present invention to be easily retrofit to sense oil or hydrocarbon fuel leakage around storage tanks by simply placing the detectors above ground immediately proximate the tank. In an original installation, however, it also can be advantageous to bury the strand portion of detector assembly 21 and its mechanically coupled absorber-expanders 31 so that direct contact and more rapid absorption occurs.

As the leaking fuel is removed by absorption, evaporation and similar atmospheric and/or remediation steps, the hydrocarbon absorbed by Red Silicone Rubber absorber-expander 31 will also desorb from or diffuse or evaporate out of the absorber-expander. This desorption gradually causes contraction of the absorber-expander and the microbending of fiber 22 diminishes. Depending upon the location of absorbent-expander 31, virtually complete desorption of hydrocarbon analyte from the Red Silicone Rubber will occur. In below-ground installations, this process takes longer, but detector apparatus 24 can sense not only the presence of hydrocarbon, but also the degree of microbending, and accordingly the concentration of the hydrocarbon analyte. Thus, when the process starts to reverse itself, detector 24, as well as the OTDR, can detect or "see" the reduction in microbending as analyte is desorbed from absorber-expander 31. Accordingly, after remediation has been completed, the new level of light transmitted along fiber 22 can be used as a new detection threshold, which can be periodically lowered to reflect continuing desorption of the hydrocarbon from the absorber, and any new leak will cause the absorber-expander to begin to expand again, producing microbending and dropping of the light intensity below the threshold. In above-ground installations, Red Silicone Rubber expander-absorbers 31 will return to their original condition with very little hysteresis.

In FIG. 2A, an alternative embodiment is shown in which fiber optic strand 22a is mechanically coupled to Red Silicone Rubber absorber-expander 31a by a containment staple 32a. Absorber-expander 31a is shown with a rectangular cross-section which presents more surface area for contact with hydrocarbon 33a. Again, expansion of the absorber-expander pushes fiber 22a to the left in FIG. 2A around opposite sides of staple 32a to create a detectable microbend.

In FIG. 2B, still a further alternative embodiment is illustrated in which rectangular absorber-expander 31b is coupled to fiber optic strand 22b by a trapezoidal-shaped containment or coupling ring 32b. In order to protect strand 22b against damage during handling, a flexible caulking compound 36 has been applied over the strand 22b. Caulking 36 does not function as an expander, nor is it used to mechanically contain or restrain the fiber. It merely functions to provide abrasion and installation handling protection and to adhere the fiber to the expander as a unit. It is not even essential that the caulking be resistant to hydrocarbon fuels, since once in place the optical fiber is not routinely exposed to being damaged. The preferred caulking material 36 is an RTV adhesive silicone sealant Dow-Corning 748.

In order to illustrate the substantially hysteresis-free cycling potential of methyl-terminated, silica and iron oxide filled silicone rubber, the following is an example using an absorber-expander constructed as shown in FIG. 1.

EXAMPLE 1

A Red Silicone rubber absorber-expander and having a diameter of ⅜ inches, a length of 1.0 inches was attached to a 100/140 optical fiber. A 4100 mCd LED was used as a source and photo diode used as a detector. The absorber-expander was placed in a pool of standing gasoline with the absorber immersed by about 0.001 inches 10 minutes. The light signal measured by the sensor was initially 2 volts and after 10 minutes had dropped to 1.1 volts. The absorber-expander was then removed from the gasoline and allowed to desorb for 150 minutes. The measured light signal increased to 2 volts. The same absorber-expander was cycled 8 times for the same length absorption desorption cycles, and on the last cycle the measured light signals were within 99% of the first cycle.

EXAMPLE 2

The same assembly as described in Example 1 was placed in a pool of water and allowed to stand for 1000 minutes. Light intensity readings were taken every 100 minutes as follows:

1. 2 volts
2. 2 volts
3. 2 volts
4. 2 volts

The detector was then placed in a pool of diesel oil and after 30 minutes the sensed flux had dropped to 28%. The detector was then removed from the oil and allowed to stand in air for 400 minutes until the light measured by the detector increased to 95. At this point, the detector was placed again in the pool of water for 1000 minutes and the light transmission continued to improve up to approximately 99%.

EXAMPLE 3

The assembly of Example 1 was positioned inside a metal container and buried in uncontaminated soil. The container was 12 inches by 24 inches and 4 inches deep. At one end of the container, 3 cubic centimeters of gasoline was poured slowly into the container and measurement of the light signal at the detector yielded the following:

| | | |
|---|---|---|
| 1. | 0 minutes | 2 volts |
| 2. | 30 minutes | 1.9 volts |
| 3. | 60 minutes | 1.6 volts |
| 4. | 90 minutes | 1.4 volts |

Referring now to FIG. 3, an alternative embodiment of the apparatus and method for detecting hydrocarbon analytes is shown. In FIG. 3, light source 41 is coupled to a plurality of optical fibers, in this case three fibers 42, 43 and 44. Mechanically coupled to fibers 42, 43 and 44 are absorber-expanders 46, 47 and 48 which are each capable of multiple reversible expansion and contraction cycles upon absorption and desorption of hydrocarbon analytes. Detectors 51, 52 and 53 are optically coupled to fibers 42, 43 and 44, in this case at end opposite source 41. The detectors in turn are electrically connected by conductors 54 to a calculating chip or computer 56 for receipt of signals from the detectors.

As will be seen, each of the absorber-expanders 46–48 is connected to their respective fiber optic fibers by a plurality of coupling rings 57. The use of a plurality of rings as a coupling mechanism around the optical fiber has the effect of increasing the sensitivity of each sensor element. The additional rings cause the system to function on the same basis as a so-called multiple-pass spectrometer. That is, the flux in the optical fiber is utilized repeatedly, in this case three times, as it passes through each "microbent" section of the optical fiber. The improvement in signals is approximately equal to the product of the effect of each ring 57 on the optical fiber.

In the sensor assembly of FIG. 3, it is preferable that absorber-expanders 46–48 be formed of rubber polymers which will absorb different hydrocarbon fuels and expand by amounts which are sufficiently different to enable assembly of expanders 58 to distinguish between different hydrocarbon fuels. Thus, expander 46 may advantageously be provided as Red Silicone Rubber, while expander 47 is Norprene rubber and expander 48 can be Latex rubber.

A mathematical formula has been derived which uses as input signals, the time rates of expansion of the absorbers to determine which hydrocarbon is present. For example, software such as MATHEMATICA algebraic software can be used to generate an algorithm which will fit into a calculator chip.

Detectors 51–54, therefore, can provided outputs to computer or calculator chip 56 in which the expansion of all three expander-absorbers in the presence of an unknown hydrocarbon fuel can be compared, and the relative expansion rates used to distinguish the hydrocarbon fuel present at assembly 58.

The following Table 1 shows the expansion rates for each absorber material for the three most common hydrocarbon fuels.

TABLE 1

| | Gasoline | Diesel | Jet-A |
|---|---|---|---|
| Red Silicone Rubber | 27 | 6 | 11 |
| Norprene Rubber | 16 | 3 | 7 |
| Latex Rubber | 20 | 4 | 2 |

In FIG. 4, the detector apparatus of the present invention includes a plurality of absorbers-expanders 61, 62 and 63 mechanically coupled by a wire wrap element 64 to optical fiber 66 to form a sensor node assembly, generally designated 67. Each of the absorber-expanders is coupled by a plurality of wraps of wire members 64 so as to enhance sensitivity in a manner described above, and further the presence of three sensor absorbers in series on the same optical 66 increases the sensitivity of node 67.

In the assembly of FIG. 4, source 68 transmits light through fiber branch 66a of optical fiber 66 to a splitter 69 and a detector, not shown, is optically coupled to the opposite end 71 of fiber 66 and formed to sense the decrease in intensity produced by microbending at node 67. It is contemplated that there will be a plurality of nodes 67 located in series along fiber 66. Accordingly, determination of which node 67 along the optical fiber is producing microbending can be accomplished by providing an optical time domain reflectometry (OTDR) back-scatter measuring device 72, which is coupled by fiber branch 66b to optical splitter 69, in a manner well-known in the art. A computing device or computer 73 can be coupled to OTDR detector 72 by conductor 74 for receipt of signals therefrom. Thus, the OTDR detector senses the backward propagation of Raleigh scattered optical flux as a result of microbending of the fiber. This allows a determination to be made by computer 73 of the location along the microstrand of the sensing node at which microbending is occurring. The detector end 71 of the strand is used as an inexpensive sentinel, only for the purpose of alerting personnel of a problem, whereupon an OTDR (very expensive) is brought into use for locating and monitoring the analog behavior of each sensor.

The use of OTDR to locate the sensor causing a light transmission decrease can be applied to virtually all of the illustrated detectors when multiple detector nodes are present in series on the same fiber or fibers.

In the embodiments of the present invention shown in FIGS. 5, 5A and 5B other manners of mechanically coupling an absorber-expander to an optical fiber in a way which will produce a decrease in light transmission on absorption of a hydrocarbon is shown. The optical fiber in FIG. 5 is comprised of a first fiber portion 81 and a second fiber portion 82, which are mounted in a framework 83 so that the opposed ends 86 and 87 are axially aligned. Source 88 will therefore transmit down first fiber portion 81 light flux which is transmitted across gap 89 to second fiber portion 82 and thereafter to detector 91. An absorber-expander 92 is positioned between framework 93 and the optical fiber, in this case the second fiber portion 82. Framework 83 is preferably an open framework which provides easy access of liquid and vapor hydrocarbon fuels to absorber-expander 92.

Upon absorption of the hydrocarbon into absorber-expander 92, the expansion will cause transverse or lateral displacement of second optical fiber portion 82, which results in an axial misalignment of ends 86 and 87 so that the light transmitted along fiber 81-82 diminishes intensity.

Aperture 89, however, can be influenced by humidity in the form of condensation in the aperture during temperature decreases. In order to eliminate such condensation problems, the assembly of FIG. 5 includes a tubular shielding element 93 which loosely receives the ends 86 and 87 of fiber portions 81 and 82. Disposed in tube 93 can be a stable encapsulating liquid 94, such as silicone oil. It is preferable that tubular shielding member 93 be of sufficient size so that silicone oil 94 will be trapped between the fiber and tube by surface tension forces. Thus, no enclosure is required between tube 93 and end 87 of second fiber portion 82, which is free to be displaced transversely relative to end 86 of first fiber portion 81. This assembly, with the shielding tube and stable inert oil, will keep condensation from occurring at gap 89 and cause the transmission across the gap to be the same except for axial misalignment of fiber portions of 81 and 82 caused by expansion of member 92.

Another feature of the assembly of FIG. 5 is that expander 92 can be moved by the user from its solid line position to the position shown in dotted lines in FIG. 5. The position along frame 83 of expander 92 can be adjusted to adjust the sensitivity of the detector assembly. In the solid line position of FIG. 5, absorber-expander 92 will produce greater lateral deflection for each unit of expansion than will occur in the dotted line position in FIG. 5 due to its position close to fiber support point 96 on frame 83. Thus, the combination of varying the point at which expansion is applied relative to the support point 96 and the rather rapid light transmission drop produced by misalignment, enhance the signal-to-noise ratio of the assembly over the microbending detectors described above. Again, however, Red Silicone Rubber has the advantage of being reversible substantially without degradation and hysteresis loss in the assembly of FIG. 5.

The optical fiber detector assembly of FIGS. 5A and 5B also includes a firsts fiber portion 81a and a second fiber portion 82a, which has axially aligned opposed ends 86a and 87a. Source 88a will therefore transmit down first fiber portion 81a light flux which is transmitted across gap 89a to second fiber portion 82a and thereafter to detector 91a. An absorber-expander 92a is positioned between opposed, fixed support surfaces 93a and 93b and has optical fiber 81a, 82a cast in it.

As will be seen from FIGS. 5A and 5B, the preferred form of absorber-expander 92a is to include two off-set masses which are relatively thin in cross section so that upon absorption of the hydrocarbon into absorber-expander 92a, the expansion will cause transverse or lateral displacement of optical fiber portions 81a, 82a in opposite directions. This is shown in dotted lines in FIG. 5A and results in an axial misalignment of ends 86a and 87a so that the light transmitted along fiber 81a, 82a diminishes in intensity.

In the assembly of FIGS. 5A and 5B, fiber 81a, 82a can be cast into the absorber-expander body and then slit at 89a from one side of body 92a. More accurately, fiber 81a, 82a is notched while in the body 92a and then cleaved at the notch to form slit 89a. This approach eases manufacture and produces an assembly in which gap 89a is not easily influenced by humidity in the form of condensation in the aperture during temperature decreases. The slit in body 92a produced by the notching tool closes upon removal from the absorber-expander.

A temperature compensated form of the detector of the present invention is shown in FIG. 6. Light source 101 transmits a signal down optic fibers 102 and 103 and absorber-expander 104 is mechanically coupled to fiber 102 by ring 107. A temperature compensating member 106 is mechanically coupled by ring 108 to fiber 103. Detectors 109 and 111 sense light transmission intensity and are input through conductors 112 to a computer or calculator chip 113.

In the assembly of FIG. 6, absorber-expander 104 in the sensing node, generally designated 114, can be Red Silicone Rubber while the other member 106 is a material selected as a reference material that will expand as a function of temperature in a manner which is known in relationship to the expansion of Red Silicone Rubber. The second member 106, however, is also selected so that it will not absorb to any significant degree or expand in the presence of hydrocarbon fuels.

One material suitable for use as the second or temperature compensating member 106 is Buna-N rubber. The temperature co-efficients of expansion of Red Silicone Rubber and Buna-N rubber are very similar (namely, 0.00032 and 0.00035, respectively) and by properly dimensioning physical sizes of members 104 and 106 the temperature expansion effects can be made to be substantially identical. Since hydrocarbons will effect only sensor element 104, the result will be a finite "difference" signal only when the hydrocarbon fuel is present at sensor node 114. Thus, two fiber optic signal channels can be used and compared to determine more accurately the value of the vapor or liquid density which has caused absorber expansion by being able to subtract out, or ratio out, the temperature expansion effects.

As will be appreciated, nodes identical to node assembly 114 can be positioned along the two-channel fiber optic assembly of FIG. 6 in a manner similar to that above described. When multiple sensor nodes are present, an optical time domain reflectometry detector would be employed to determine the location as between sensing nodes. Computer 113 would be used to obtain a temperature-insensitive value for the vapor or liquid sensed at the sensor node. Other assemblies of absorber-expanders and temperature expanders can be provided so that the mechanical components have motions which balance out to zero net displacement, while hydrocarbon absorption produces unbalanced expansion. Such techniques are particularly easily adapted to fiber misalignment detector assemblies and are analogous to Wheatstone bridge hulling circuits.

A combination of optical fibers and absorber-expanders also can be used without optical time domain reflectometry to provide location information by using sensor assembly nodes capable of providing digital output information. In FIG. 7, a circular oil tank 121 has a plurality of sensor assemblies or nodes 122 positioned around the periphery of the tank. In this case, there are 13 sensor nodes with 12 being positioned proximate the periphery and 1 proximate the center of the tank, but it will be appreciated that many other configurations are possible. Each sensor node 122 is connected to four optical fibers 123-126. Mechanically coupled to at least one of fibers 123-126 at each sensor node 122 is an absorber-expander 131, for example, by a ring 132 or similar coupling as above described. The number of absorber-expanders coupled to the optical fibers, and the optical fibers which the absorber-expanders are coupled to are selected to provide a distinctive digital output for each node 122 of the series sequence of sensor nodes.

Optically coupled to fibers 123-126 is a source of light flux 133 and light intensity detectors 136-139. A computer assembly or calculating chip 141 can be electrically connected to detectors 136-139 by conductor means 142. In the assembly of FIG. 7, however, detectors 136 through 139 merely measure the transmitted light intensity; they do not act as back-scatter or optical time domain locating detectors.

Upon the occurrence of a hydrocarbon fuel leak 143, microbending will occur at sensor node 122a. Absorbers 131 at sensor node 122a will cause microbending of optical fibers 123 and 124. The light transmitted through optical fibers 126 and 127, however, will not be effected. Detectors 138 and 139 will sense decrease in light intensity transmitted along fibers 123 and 124, and detectors 136 and 137 will sense a continuing unchanged light intensity. Computer 141 can immediately determine that the only location along the series of sensor nodes 122 which absorber-expanders 131 are coupled to both optical fibers 123 and 124 is at sensing node 122a. Thus, the location of leak 143 can be readily determined by simply sensing a decrease in light transmission at the combination of fibers 123 and 124, with no decrease in light transmission of fibers 125 and 126. This node has the digital code; 1100, which is equivalent to the number 3.

A digital output, therefore, can be created simply by coupling absorber-expanders to a plurality of optical fibers in a manner which provides each sensing node 122 with its individual and unique combination of sensors. The number of sensing nodes which can be created is equal to two to the power of the number of fibers less one. The case in which no absorber-expanders are secured to the fibers cannot be used. Missing in FIG. 7 are two digital locations; 1010 and 0101.

One of the advantages of the detection apparatus and method of present invention is that the detector can be operated either as an unbiased or a biased detector. Referring to FIG. 10, an unbiased detector will have a Q or quiescent point at zero fiber displacement. When microbending occurs, the transmission falls from $Q_u$, for example, to the point $P_u$ as a result of microbending or displacement of the fiber.

For biased sensors, $Q_B$ is shown in FIG. 10 for a transmission of flux equal to about 0.7 of the unbiased condition, and this condition can be produced by microbending of the fiber through a biasing displacement of $x_1$. When further microbending occurs as a result of absorber-expander expansion, transmission is reduced from $Q_B$ to $P_B$ while fiber displacement increases to $x(s)$.

In serial sensor node arrangements which employ optical time domain location, it is necessary to have almost zero insertion loss, that is, to use unbiased sensors with $Q_B$ located at maximum transmission and zero displacement. When insertion loss is not a factor of importance, particularly in so-called point sensors, biasing of the sensor can be employed to increase the signal-to-noise ratio and sensor sensitivity. Such an effect can be used alone or in combination with multiple coupling rings, as above described.

FIGS. 8 and 9 show one form of sensor biasing which can be used in the detector assembly method of the present invention. An optical fiber 151 has an absorber-expander 152, such as Red Silicone Rubber, coupled thereto by a band 153. Band 153 preferably is formed of a material that can be plastically deformed so as to effect biasing of the sensor. Thus, band 153 can have a general trapezoidal shape with one leg 154 extending around the expander-absorber 152 and a second leg 156 extending around the absorber-expander in the other direction. Legs 154 and 156 can be separated from each other to cause microbending of fiber 151. Thus, as leg 156 is moved from the solid line position in FIG. 8 to the phantom line position, optical fiber 151 will experience a microbend to the phantom line position of FIG. 8. Additionally, some deformation occurs of absorber-expander 152. Since the containment ring 153 is plastically deformable, once the legs are separated, the microbend biasing of the sensor will remain. It will be appreciated that other biasing structures are suitable for use in the present invention, but the coupling ring 153 allows for easy biasing by simply separating legs 154 and 156 until the desired amount of biasing has been produced. This will cause the biased quiescent operating point, $Q_B$, to be positioned in a manner as shown in FIG. 10.

The hydrocarbon full detector assembly and method of the present invention, therefore, employ a hydrophobic, hydrocarbon absorber which will expand significantly and is capable of multiple cycles of absorption and desorption without breaking down and losing its structural integrity. Methyl terminated, silica and iron oxide filled, dimethyl polysiloxane has these characteristics and can be mechanically coupled to an optical fiber to cause a decrease in light transmission upon expansion of the absorber. Microbending or axial fiber misalignment can be detected by sensing flux transmission decreases, and OTDR back-scatter or digital sensing node configurations used to determine location. Sensitivity can be enhanced by coupling techniques and biasing of the quiescent operating point.

What is claimed is:

1. A method for detecting the presence of a hydrocarbon analyte in at least one of a liquid and a vapor state comprising the steps of:

positioning an optical fiber in a location for detection of said hydrocarbon with an absorber-expander member mechanically coupled to said fiber to produce a change in light transmission in said fiber upon absorption of said hydrocarbon analyte by, and expansion of, said absorber-expander member, said absorber-expander being hydrophobic and being selected to have multiple reversible expansion and contraction cycles upon absorption and evaporation of said hydrocarbon analyte by said absorber-expander; and detecting a change in light transmission in said fiber.

2. The method as defined in claim 1 and the additional step of:

detecting the location along said fiber at which said absorber-expander causes a change in light transmission.

3. The method as defined in claim 1 and the additional step of:

prior to said positioning step, coupling said absorber-expander member to said fiber to produce microbending of said fiber, and during said detecting step, detecting the location of a microbend in said fiber.

4. The method as defined in claim 1 wherein, said selecting step is accomplished by selecting as an absorber-expander a methyl terminated, silica and iron oxide filled, dimethyl polysiloxane polymer.

5. The method as defined in claim 1 wherein, prior to said positioning step, said absorber-expander is coupled to a first portion of said optical fiber to displace said first portion relative to a second portion of said optical fiber to produce axial misalignment in said optical fiber.

6. A method of making a hydrocarbon detection apparatus comprising the steps of:

selecting a silicone rubber member as an absorber-expander for a hydrocarbon in at least one of a liquid state and a vapor state, said silicone rubber member being selected to absorb and expand in the presence of said hydrocarbon and to recover and contract to a substantially undegraded condition in the absence of said hydrocarbon;

mechanically coupling said silicone rubber member to a fiber optic strand in a manner producing one of microbending and axial misalignment of said strand upon expansion of said silicone rubber member; and optically coupling detection apparatus means to said strand for detection of the occurrence of decreased light transmission along said strand.

7. The method as defined in claim 6 wherein, said selecting step is accomplished by selecting as an absorber-expander a methyl terminated and iron oxide and silica filled silicone rubber member.

8. The method as defined in claim 7 wherein, said mechanically coupling step is accomplished by encircling said fiber optic strand with a rigid member and coupling said rigid member to said silicone rubber member for relative displacement of said rigid member and said fiber optic strand against each other to produce microbending.

9. The method as defined in claim 7 wherein, said mechanically coupling step is accomplished by encircling both said fiber optic strand and said silicone rubber member with a rigid member having a relatively short dimension along said fiber optic strand.

10. The method as defined in claim 9 wherein, said rigid member is provided by at least one ring.

11. The method as defined in claim 9 wherein, said rigid member is provided by a wire wound in a spiral around said silicone rubber member.

12. The method as defined in claim 6 wherein, said selecting step is accomplished by selecting a solid silicone rubber member which absorbs hydrocarbon fuels in both a liquid state and a vapor state.

13. The method as defined in claim 6 wherein, said selecting step is accomplished by selecting a silicone rubber member which expands upon absorption of hydrocarbons and contracts upon the emission of absorbed hydrocarbons by an amount proportional to the quantity hydrocarbon contacting said silicone rubber member.

14. The method as defined in claim 6 wherein, said mechanically coupling step is accomplished by encircling said strand and a portion of said rubber member by staple means.

15. The method as defined in claim 6 wherein, said mechanically coupling step is accomplished by coupling said rubber member to said strand in a manner producing a biasing microbend in said strand prior to any absorption of hydrocarbon by said silicone rubber member.

16. The method as defined in claim 6 wherein, said optically coupling step is accomplished by optically coupling detection means to said strand suitable for detecting the location of a microbend along said strand.

17. The method as defined in claim 6 wherein, said mechanically coupling step is accomplished by coupling a plurality of silicone rubber members to a plurality of fiber optic strands at discrete locations producing a digital detection array; and said optical coupling step is accomplished by coupling a detection means to said plurality of strands forming said digital detection array suitable for determining the location of microbending based upon sensing of the presence of microbending on combinations of strands.

18. The method as defined in claim 6 and the step of:

mechanically coupling a temperature control member to a second fiber optic strand, said temperature control member expanding and contracting in proportion to temperature changes by an amount substantially known relative to the expansion and contraction of said silicone rubber member and said temperature control member maintaining its dimensional stability when in contact with said hydrocarbon rubber member for the same temperature changes;

optically coupling said second fiber optic strand to said detection means; and positioning said second fiber optic strand so that said temperature control member is closely proximal said silicone rubber member.

19. The method as defined in claim 6 wherein, said mechanically coupling step is accomplished by mechanically coupling a plurality of absorber-expander members to a single fiber optic strand along a length thereof to provide a series detection array, said absorber-expanders having differing expansion rates upon absorption of a given hydrocarbon.

20. The method as defined in claim 6 wherein, said mechanically coupling step is accomplished by mechanically coupling a plurality of discrete absorber-expanders to a plurality of fiber optic strands to produce a parallel detection array, said absorber-expanders having differing expansion rates upon absorption of a given hydrocarbon.

21. The method as defined in claim 6 wherein, said mechanically coupling step is accomplished by mechanically coupling said silicone rubber member to said fiber optic strand to produce microbending of said strand with coupling means multiplying the amount of microbending of said strand upon expansion of said silicone rubber member.

22. The method as defined in claim 21 wherein, said mechanically coupling step is accomplished by mounting a plurality of side-by-side strand-encircling rigid members on said fiber optic strand.

23. The method as defined in claim 6 wherein, said fiber optic strand is provided by two strand portions axially aligned for transmission of a signal from one strand portion to the other; and said mechanically coupling step is accomplished by coupling said silicone rubber member to one of said strand portions of said fiber optic strand for displacement of said one of said strand portions transversely relative to the other of said strand portions to produce axial misalignment.

24. The method as defined in claim 6 wherein, said optic fiber strand is provided by two strand portions axially aligned for transmission of a signal from one strand portion to the other; and said mechanically coupling step is accomplished by coupling said silicone rubber member to both of said strand portions for displacement of said strand portions in opposite directions relative to each other.

25. A detection apparatus for detecting the presence of at least one of a liquid hydrocarbon and a hydrocarbon vapor comprising:

an optical fiber;

an absorber-expander member mechanically coupled to said optical fiber to produce a change in transmission of light along said optical fiber upon absorption of said hydrocarbon, said absorber-expander being formed of a hydrophobic hydrocarbon-absorbing rubber material selected to expand upon absorption of said hydrocarbon and selected to retain sufficient structural integrity to permit repetitive use; and detection apparatus optically coupled to said optical fiber for detection of a change in light transmission along said fiber.

26. The apparatus as defined in claim 25 wherein, said rubber material is selected from the group consisting of silicone rubber, latex rubber and Norprene rubber.

27. The apparatus as defined in claim 26 wherein, said rubber material is dimethyl polysiloxane having silica and iron oxide fillers therein.

28. The apparatus as defined in claim 25 wherein, said absorber-expander member is mechanically coupled by a rigid member extending from said absorber-expander member to said optical fiber to produce microbending of said optical fiber.

29. The apparatus as defined in claim 28, and adhesive means coupling said rigid member to said absorber-expander member.

30. The apparatus as defined in claim 28 wherein, said rigid member encircles said optical fiber.

31. The apparatus as defined in claim 30 wherein, said rigid member encircles both said optical fiber and said absorber-expander member.

32. The apparatus as defined in claim 28 wherein, said rigid member is provided by a ring encircling said optical fiber and a portion of said absorber-expander member.

33. The apparatus as defined in claim 32 wherein, said optical fiber and said absorber-expander are both cylindrical and oriented with central longitudinal axes substantially parallel and said ring is substantially circular and has a width dimension along said optical fiber which is relatively thin.

34. The apparatus as defined in claim 33, and a plurality of spaced apart, side-by-side relatively rigid rings each encircling both said optical fiber and said absorber-expander member.

35. The apparatus as defined in claim 28 wherein, said absorber-expander member is mechanically coupled to said optical fiber by a staple.

36. The apparatus as defined in claim 28 wherein, said absorber-expander member is mechanically coupled to said optical fiber by a strand wound around both said optical fiber and said absorber-expander member.

37. The apparatus as defined in claim 36 wherein, said strand is a metallic wire.

38. The apparatus as defined in claim 25, and a plurality of absorber-expander members each formed as defined for the first-named absorber-expander, said absorber-expanders each being mechanically coupled to said optical fiber at spaced apart positions along the length of said optical fiber in a manner producing microbending of said optical fiber upon absorption of said hydrocarbon.

39. The apparatus as defined in claim 25 wherein, said absorber-expander member will absorb gasoline, Jet-A fuel and diesel fuel.

40. The apparatus as defined in claim 39 wherein, said absorber-expander member will absorb said hydrocarbon in both liquid and vapor states.

41. The apparatus as defined in claim 25 wherein, said optical fiber is provided with a first fiber portion having a first end and a second fiber portion having a second end spaced apart from and optically aligned with said first end for transmission of light from said first fiber portion to said second fiber portion; and said absorber-expander being mechanically coupled to one of said first fiber portion and said second fiber portion to produce displacement of said one laterally relative to the other of the fiber portions by an amount affecting light transmission along said fiber portions.

42. The apparatus as defined in claim 41 wherein, said absorber-expander is coupled to both said first fiber portion and said second fiber portion and supported for displacement of said first fiber portion and said second fiber portion in opposite directions.

43. The apparatus as defined in claim 25 wherein, said absorber-expander member is mechanically coupled to said optical fiber by a coupling assembly producing displacement of said optical fiber by an amount greater than the amount of expansion of said absorber-expander member.

44. The apparatus as defined in claim 25 wherein, said absorber-expander member is mechanically coupled to said optical fiber in a manner biasing said optical fiber with a pre-established microbend at said absorber-expander member.

45. The apparatus as defined in claim 44, and mounting apparatus mechanically coupling said absorber-expander to said optical fiber, said mounting apparatus producing said microbend.

46. The apparatus as defined in claim 45 wherein, said mounting apparatus is provided by a ring-like member having a central portion extending around said optical fiber and having a pair of spaced apart leg portions engaging said absorbent-expander member, said leg portions being movable between selected fixed relative positions to pull said central portion toward said optical fiber and establish the amount of microbending biasing said optical fiber.

47. The apparatus as defined in claim 25 wherein, said absorber-expander member is formed of a rubber material having a known rate of expansion for each of two differing hydrocarbon fuels; and further comprising:

an additional optic fiber having an additional absorber-expander member formed of a hydrocarbon-absorbing rubber member mechanically coupled thereto in a manner producing a change in light transmission upon expansion of said additional hydrocarbon-absorbing rubber member, said additional absorber-expander member having a known rate of expansion for each of said two differing hydrocarbon fuels, which rates of expansion differ from the rates of expansion of the first named absorber-expander member;

said additional absorber-expander member being positioned proximate said first named absorber-expander member; and said detection apparatus being optically coupled to said additional optical fiber and being formed to quantify the amount of change of light transmission produced upon expansion of the absorber-expanders and including computational apparatus for comparison of the quantity of change of transmission of light from the two optical fibers to determine the hydrocarbon fuel being detected.

48. The apparatus as defined in claim 25, and an additional optical fiber having an additional rubber member mechanically coupled thereto in a manner substantially identical to coupling of said absorber-expander member to the first-named optical fiber;

said additional rubber member having a thermal coefficient of expansion having a known relationship to a thermal coefficient of expansion of said absorber-expander member, and said additional rubber member being substantially incapable of absorbing hydrocarbons absorbed by said absorber-expander member;

said additional rubber member being positioned proximate said absorber-expander member; and said detection apparatus being optically coupled to said additional optical fiber and being formed to quantify the amount of change in light transmission produced by expansion of said absorber-expander member and said additional rubber member, and including comparison and computational apparatus for comparing said amount of change and subtracting temperature induced change.

49. The apparatus as defined in claim 25, said optical fiber has a plurality of substantially similar absorber-expander members mechanically coupled to said optical fiber along a length thereof;

a plurality of additional optical fibers positioned proximate the first-named optical fiber;

a plurality of additional absorber-expander members substantially similar to the first-named absorber-expander member and mechanically coupled to each of said additional optical fibers;

said first-named absorber-expander members and said additional absorber-expander members being coupled along their respective optical fibers in a digital detection array with a different combination of absorber-expanders at each of a plurality of detection sites;

said detection apparatus being coupled to each of said additional optical fibers; and computer means coupled to said detection apparatus and formed to be responsive to combinations of signals from said detection apparatus to determine the location of a detected hydrocarbon.

50. A hydrocarbon detection apparatus comprising:

an optical fiber;

a methyl terminated, silica and iron oxide filled dimethyl polysiloxane rubber member mechanically coupled to said optical fiber to produce microbending of said fiber upon absorption of at least one of a liquid hydrocarbon and a hydrocarbon vapor by said red silicone rubber; and microbend detection apparatus optically coupled to said fiber to detect the presence of a microbend in said fiber.

* * * * *